United States Patent [19] [11] 4,329,473
Almquist et al. [45] May 11, 1982

[54] OXOALKANOIC ACID DERIVATIVES AS INHIBITORS OF ANGIOTENSIN CONVERTING ENZYME

[76] Inventors: Ronald G. Almquist, 2463 Burnham Way, Palo Alto, Calif. 94303; Joseph I. De Graw, 880 Hanover, Sunnyvale, Calif. 94087

[21] Appl. No.: 219,885

[22] Filed: Dec. 24, 1980

Related U.S. Application Data

[63] Continuation-in-part of Ser. No. 44,685, Jun. 1, 1979, abandoned.

[51] Int. Cl.³ .................. C07D 207/12; C07D 207/16; C07D 401/12; C07D 405/12
[52] U.S. Cl. ................................. 546/281; 424/263; 424/274; 546/272; 548/468; 548/517; 548/533; 549/448; 549/452
[58] Field of Search ..................... 260/326.36, 326.43; 546/281

[56] References Cited
U.S. PATENT DOCUMENTS 3,141,024  7/1964  Houssin .......................... 260/326.43
4,040,889  9/1977  Ondetti et al. ..................... 260/326.2
4,091,024  5/1978  Ondetti ........................... 260/326.25
4,113,715  9/1978  Ondetti et al. ................... 260/112.5 R
4,116,962  9/1978  Ondetti et al. ..................... 260/326.2
4,127,729 11/1978  Ondetti ............................... 560/147
4,128,721 12/1978  Ondetti ............................... 560/16
4,154,934  5/1979  Bernstein et al. ................. 260/326.25
4,154,936  5/1979  Ondetti et al. ..................... 424/274
4,154,946  5/1979  Ondetti et al. ................... 260/326.25

OTHER PUBLICATIONS

Ondetti et al., Science, vol. 196, p. 441, (1977).
Cushman et al., Biochemistry, vol. 16, p. 5484, (1977).
Atkinson et al., Lancet, p. 557, (1979).

Primary Examiner—Mary C. Lee

[57] ABSTRACT

This invention relates to novel analogs of proline terminal tripeptides and related compounds and is typified by

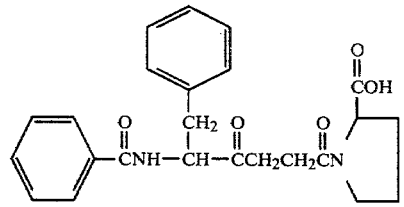

5-Benzamido-4-oxo-6-phenylhexanoyl-L-proline The compounds are potent inhibitors of angiotensin converting enzyme and as such are useful as antihypertensive agents.

22 Claims, No Drawings

OXOALKANOIC ACID DERIVATIVES AS INHIBITORS OF ANGIOTENSIN CONVERTING ENZYME

ORIGIN OF INVENTION

The invention described herein was in part made in the course of work under a grant from the National Institutes of Health, Department of Health and Human Services.

This application is a continuation-in-part of copending application, Ser. No. 44,685 filed June 1, 1979, now abandoned.

BACKGROUND OF INVENTION

Angiotensin converting enzyme is responsible for the conversion of the decapeptide angiotensin I to the potent vasopressor, angiotensin II, an octapeptide. Peptide compounds derived from snake venom and ranging from pentapeptide to nonapeptide have been found to be potent inhibitors of the converting enzyme, see, for example, L. J. Green, J. M. Stewart and S. H. Ferreira, Pharmacol. Res. Comm., 1, 159 (1969); M. A. Ondetti, N. J. Williams, E. F. Sabo, J. Pluscec, E. R. Weaver and O. Kocy, Biochemistry, 10, 4033 (1971). The further work of D. W. Cushman, J. Pluscec, N. J. Williams, E. R. Weaver, E. F. Sabo, O. Kocy, H. S. Cheung and M. A. Ondetti, Experientia, 29, 1032 (1973) teaches that various smaller peptides such as tripeptides also display useful inhibitory potency against the converting enzyme. For example, a tripeptide such as phenylalanyl-alanyl-proline showed a substantial degree of activity. The nonapeptide above was shown to lower blood pressure in animal models of renovascular hypertension, see, for example, S. L. Engel, T. R. Schaeffer, M. H. Waugh and B. Rubin, Proc. Soc. Exptl. Biol. Med., 143, 483 (1973); E. E. Muirhead, B. Brooks and K. K. Arora, Lab Invest. 30, 129 (1974) and in humans with various forms of hypertension, see, for example, H. Gavras, H. R. Brunner, J. H. Laragh, I. Gavras and R. A. Vukovich, New Engl. J. Med., 291, 817 (1974). The lack of oral activity, however, has limited the use of the nonapeptide as a therapeutic drug for treatment of hypertension. Thus the various peptides have not found clinical acceptance because of their apparent instability to hydrolytic media such as the various peptidases of the gut.

It is an object of this invention to provide novel compounds having potent inhibitory properties against the angiotensin converting enzyme. A further object is to provide compounds of this character which are reasonably stable to hydrolytic media and thus allow attainment of therapeutically useful levels of the compound in the blood.

SUMMARY OF INVENTION

The present invention provides novel compounds meeting the foregoing objects, said compounds being related to the above-mentioned tripeptides, but with substitution of a ketomethylene moiety in place of the amide linkage between the first and second amino acids as measured from the N-terminus of the peptide chain. This substitution confers the required hydrolytic stability to the tripeptide analogs about this important connective region. (The amide bond to the C-terminal amino acid, such as proline, is a tertiary amide bond and unreactive with the various peptidases of the gut).

The compounds of the present invention are novel proline analogs having the structure

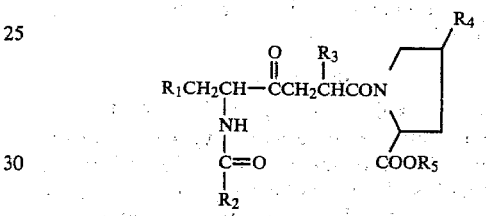

wherein $R_1$ represents aryl, e.g. phenyl 3-indolyl or pyridyl;
$R_2$ represents aryl, alkyl, alkoxy, e.g., butoxy or benzyloxy;
$R_3$ represents hydrogen or lower alkyl;
$R_4$ represents hydrogen or hydroxyl;
$R_5$ represents hydrogen or lower alkyl.

Alkyl groups, where mentioned, are intended to include straight as well as branched chain alkyl groups of from $C_1$ through $C_{10}$ such as methyl, ethyl, isopropyl, butyl, isobutyl, sec-butyl, t-butyl, pentyl, isopentyl, hexyl, 2-ethyl hexyl, heptyl and octyl, nonyl and decyl.

Examples of compounds falling within the scope of this invention are correlated with the general formula on page 5 and are listed in the following Table I.

TABLE I

| Example No. | $R_1$ | $R_2$ | $R_3$ | $R_4$ | $R_5$ |
|---|---|---|---|---|---|
| I | $C_6H_5$ | $C_6H_5-$ | H | H | H |
| II | $C_6H_5$ | $C_6H_5-$ | H | H | $CH_3$ |
| III | $C_6H_5$ | $C_6H_5CH_2O-$ | H | H | H |
| IV | $C_6H_5$ | ![pyridyl] | H | H | H |
| V | $C_6H_5$ | ![furyl] | H | H | H |
| VI | $C_6H_5$ | ![furyl] | H | H | H |
| VII | $C_6H_5$ | $o\text{-}CH_3C_6H_4-$ | H | H | H |
| VIII | $3,4(OCH_3)_2C_6H_3-$ | $C_6H_5-$ | H | H | H |
| IX | $p\text{-}C_6H_5CH_2OC_6H_4-$ | $C_6H_5-$ | H | H | H |
| X | $p\text{-}HOC_6H_4-$ | $C_6H_5-$ | H | H | H |
| XI | ![indolyl] | $C_6H_5-$ | H | H | H |

TABLE I-continued

| Example No. | $R_1$ | $R_2$ | $R_3$ | $R_4$ | $R_5$ |
|---|---|---|---|---|---|
| XII | $C_6H_5$ | $C_6H_5-$ | H | OH | H |
| XIII | $C_6H_5$ | $C_6H_5-$ | $CH_3$ | H | H |
| XIV | $C_6H_5$ | $C_6H_5-$ | $(CH_3)_2CH$ | H | H |
| XV | $C_6H_5$ | $n-C_4H_9O-$ | H | H | H |
| XVI | $C_6H_5$ | $n-C_4H_9O-$ | $CH_3$ | H | $CH_3$ |
| XVII | $C_6H_5$ | $n-C_4H_9O-$ | $CH_3$ | H | H |
| XVIII | $C_6H_5$ | $CH_3-$ | H | H | H |
| XIX | $C_6H_5$ | $n-C_5H_{11}-$ | H | H | H |
| XX | $C_6H_5$ | $n-C_7H_{15}-$ | H | H | H |
| XXI | $C_6H_5$ | $n-C_9H_{19}-$ | H | H | H |

As will be evident from the biological testing data presented below (Table II) examples of the compounds of the present invention have utility as inhibitors of angiotensin converting enzyme and thus potentially as antihypertensive agents.

Procedure A

This method was used to prepare Example I and is shown schematically below (Scheme A). An aminoacid such as phenylalanine or tryptophan is blocked on the amine nitrogen as the phthalimido (or other suitable acyl) derivative. The carboxyl moiety is activated preferably as the thiopyridine ester (or other reactive species such as acid chloride, anhydride, etc.) and the resulting compound 1 is condensed with the Grignard reagent derived from a 3-bromo-propionaldehyde ethylene acetal to form the phthalimide oxoacetal 2. Other aldehyde protecting groups such as diethyl or dimethyl acetals may be employed as well as similar derivatives derived from 3-chloro or 3-iodopropionaldehydes. The keto group of 2 is then converted to the ethylene or other alkoxyl ketal 3 followed by hydrazinolysis of the phthalimide group to yield the amino ketal acetal 4, which is directly treated with an acyl chloride (such as benzoyl) or arylsulfonyl chloride in the presence of pyridine (or other suitable acid acceptor) to form the N-blocked ketal acetal 5. Hydrolysis of the aldehyde acetal and simultaneous oxidation of the liberated aldehyde is accomplished by treatment of 5 with chromic acid in sulfuric acid or other suitable acid medium. The ketal acid 6 so obtained is further hydrolyzed with 90% trifluoroacetic acid (or other suitable acid medium) to afford the N-derivatized keto acid 7. The acid 7 is suitably activated at the carboxyl group by a variety of reagents obvious to those skilled in the art (such as cyclohexylcarbodiimide, alkoxy chloroformates, carbonyl diimidazole, etc.). The activated carboxylate is then coupled with a proline ester (such as benzyl or lower alkyl ester or N,O-ditrimethylsilylproline to give an amido ester (8). The benzyl ester is deprotected via hydrogenolysis over a palladium catalyst; lower alkyl ester is removed by mild alkaline hydrolysis and silyl ester by exposure to a mildly acidic aqueous medium. This coupling and ester cleavage process may also be extended to include hydroxy proline analogs.

SCHEME A

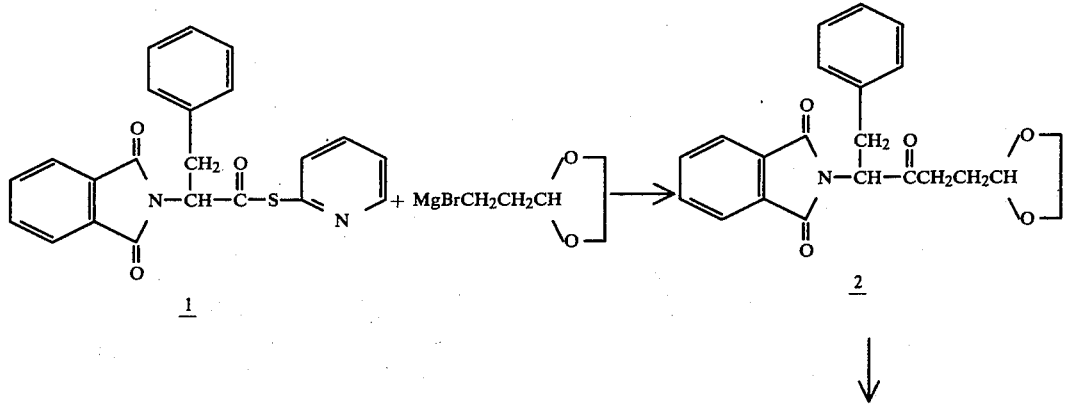

-continued
SCHEME A

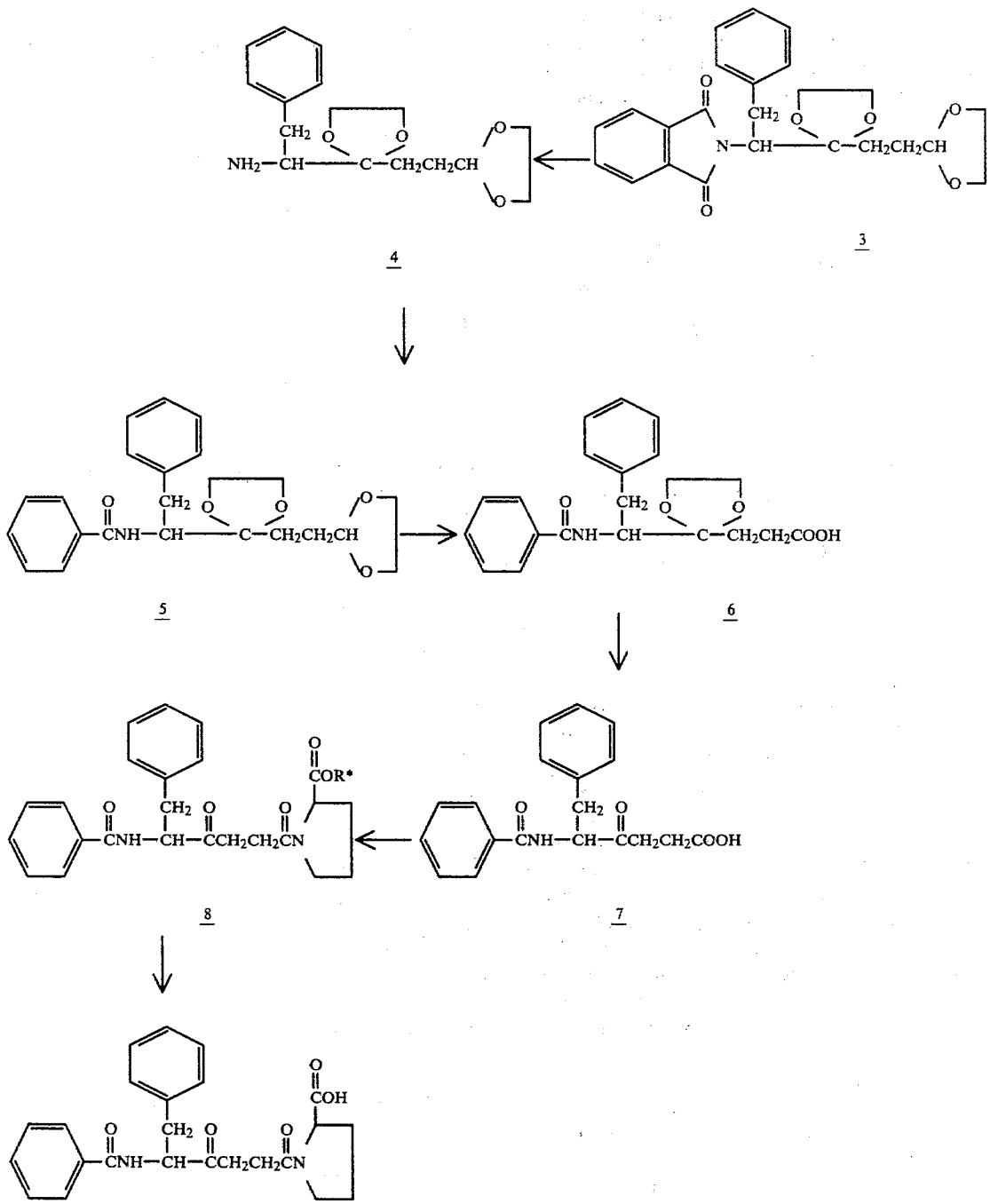

*R = benzyl, lower alkyl, or (CH$_3$)$_3$Si—

Procedure B

This method was also used to prepare Example I as well as Examples V, VII, VIII, IX, XI, XIII, XIV and XVI and is shown schematically (Scheme B). An azlactone derivative (10) of an appropriate amino acid (prepared by various methods described herein) is mixed with an equivalent of 3-carbomethoxypropionyl chloride in tetrahydrofuran followed by slow addition of triethyl amine, with cooling, to promote condensation at the α-position to afford the acyl azlactone (11). This step may be carried out with other esters of carboxypropionyl chloride and may be conducted in a variety of polar organic solvents utilizing other tertiary amines or suitable bases such as alkali metal hydrides. the acyl azlactone intermediate is then treated with a hot acetic acid-pyridine mixture to effect ring opening and decarboxylation to the 5-acylamido-4-oxohexanoate intermediate (12). The ester (12) is saponified via exposure at ordinary temperature to aqueous alkali with the aid of a polar organic co-solvent (e.g. tetrahydrofuran, methanol, ethanol) to afford the 5-acylamido-4-oxocarboxylic acid (13). The acid (13) is suitably activated at the carboxyl group and coupled with proline esters and the ester group removed (as described in Procedure A above) to afford the target 6-substituted-5-acylamido-4-oxohexanoyl prolines.

SCHEME B

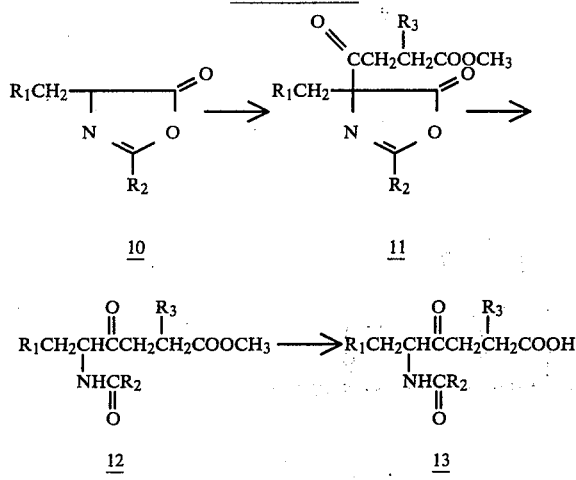

Procedure C

This method was used to prepare Examples III, IV, XV, XVIII, XIX, XX and XXI and is shown in Scheme C. A 6-substituted-5-acylamido-4-oxohexanoic acid (18) is hydrolyzed in a strongly acid medium (e.g. hydrochloric acid, sulfuric acid) with the aid of acetic acid as a co-solvent. The product, a 6-substituted-5-amino-4-oxohexanoic acid (19), is obtained as the corresponding acid salt of the 5-amino group. The amino acid 19 is then esterified in an appropriate alcohol (e.g. methanol, ethanol) with acid catalysis to prepare the aminoester (20) and isolated as the corresponding acid salt. The amino ester salt (20) is mixed with an equivalent of an appropriate acyl halide in aqueous media and the pH is adjusted to and maintained at 6.5 by addition of aqueous sodium carbonate (or other alkali metal carbonate or hydroxide). The product, a 6-substituted-5-acylamino-4-oxohexanoic acid ester (21), is saponified to the acylamino acid (22) by treatment with alkali in aqueous alcohol or other suitable aqueous, alkaline medium. The acylamino acid (22) is activated at the carboxyl group and coupled to a proline ester as described under Procedure A.

SCHEME C

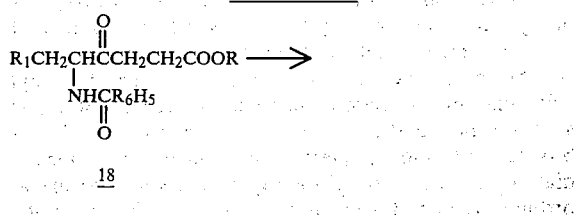

-continued
SCHEME C

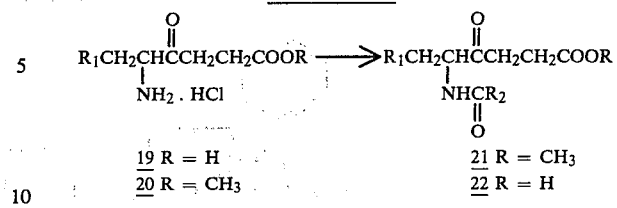

EXAMPLE I

5-Benzamido-4-oxo-6-phenylhexanoyl-L-proline (9)

Procedure A

Step 1. L-Phenylalanine-2-thiopyridine ester (1).

A mixture of N-phthaloyl-L-phenylalanine (70.9 g, 0.24 mole), phosphorous pentachloride (55.0 g, 0.26 mole) and benzene (1 liter) was stirred at 50°–55° C. for 1 hour with protection from moisture. The mixture was cooled, filtered and evaporated. The residue was dissolved in toluene (500 ml) and the solvent evaporated. The residue was then dissolved in hot benzene (200 ml) and diluted with petroleum (30°–60° C. b.p.). The crystalline precipitate was collected and dried to leave 74 g. The acid chloride so obtained (62.7 g, 0.20 mole) was dissolved in ethyl acetate (2 liter), the solution cooled (5° C.) and 2-mercaptopyridine (44.7 g, 0.40 mole) was added. The mixture was stirred for 3 hours with continued cooling, followed by storage under refrigeration for 3 days. The mixture was washed with brine (2 liter) and saturated sodium bicarbonate. The organic solution was dried, and evaporated to leave a syrup, crystallized from ether-petroleum (30°–60° C. b.p.) to afford 68.3 g (88%), m.p. 100°–103° C.

Step 2. 2-(3-Oxo-5-phenyl-4-phthalimidopentyl)-1,3-dioxolane (2).

A solution of 2-(2-bromoethyl)-1,3-dioxolane (92.3 g, 0.51 mole) in dry tetrahydrofuran (660 ml) was added over 1.5 hours to a stirred mixture of magnesium turnings (16.5 g, 0.68 mole) in dry tetrahydrofuran (25 ml) at 30°–35° C. and transferred with filtration to a dry addition funnel. One-third of this solution was added over 15 minutes to a stirred solution of N-phthaloyl-L-phenylalanine 2-thiopyridine ester (66.0 g 0.17 mole) in 660 ml of dry tetrahydrofuran with cooling to maintain the temperature at 30°–35° C. After the addition, the mixture was stirred for 2 hours at ambient temperature, followed by addition of the remaining Grignard solution in two equal portions under similar conditions. Stirring was continued for 16 hours followed by addition of saturated ammonium chloride until the cloudy mixture became clear (ca. 85 ml required). After 4 hours the mixture was filtered and the filtrate evaporated in vacuo. The residue was taken up in 1 liter of ethyl acetate and successively washed with 0.1 N sodium hydroxide and saturated brine. The organic solution was dried and evaporated to leave a residual syrup, 91.0 g. The material was purified by chromatography and recrystallized from ether-petroleum (30°–60° C. b.p.) to afford 22.3 g (35%) of white crystals, m.p. 96°–97° C.; $[\alpha]_D^{21} = -154°$ (CHCl$_3$), Calc'd (C$_{22}$H$_{21}$NO$_5$): C, 69.6; H, 5.58; N, 3.69. Found: C, 69.4; H, 5.45; N, 3.68.

Step 3. 2-(1,3-dioxolane-2)ethyl-2-(1-phthalimido-2-phenylethyl)-1,3-dioxolane (3).

A mixture of 2 (1.00 g, 2.63 mmol), dry toluene (50 ml), ethylene glycol (9 ml) and p-toluenesulfonyl chloride (40 mg) was stirred and slowly distilled. Each time 10 ml of distillate had accumulated an additional 10 ml of dry toluene was added to the reaction mixture. After 11 hours of this procedure the reaction mixture was allowed to cool and the layers were separated. The toluene layer was evaporated to a yellow syrup. This syrup was dissolved in chloroform (50 ml) and washed successively with 0.1 N NaOH (50 ml) and H$_2$O (50 ml). The chloroform solution was dried and evaporated to a pale yellow gum, 1.11 g. This gum was crystallized from ether-petroleum (30°–60° C. b.p.) to give white crystals (0.64 g, 58%), m.p. 105°–108° C. $[\alpha]_D^{20}$ −111° (CHCl$_3$); Calc'd. (C$_{24}$H$_{25}$NO$_6$): C, 68.1; H, 5.95; N, 3.31. Found: C, 68.4, H, 6.06, N, 3.22.

Steps 4–5. 2[2-(1,3-Dioxolane-2)ethyl]-2-(1-benzamido-2-phenylethyl) 1,3-dioxolane (5).

A mixture of 3 (2.00 g, 4.72 mmol), absolute ethanol (120 ml) and 97% hydrazine (1.05 ml, 33.0 mmol) was stirred at reflux for 15 hours. The mixture was evaporated and the residue partitioned between chloroform (150 ml) and 0.3 N sodium hydroxide (200 ml). The chloroform extract was washed with water (200 ml), dried and evaporated to leave the amino ketal 4 as a clear syrup, 1.30 g. An ice cold solution of the amine in pyridine (75 ml) was treated with benzoyl chloride (0.62 ml, 5.35 mmol) and the mixture kept at ambient temperature for 3 days. The solvent was evaporated in vacuo and the residue was dissolved in chloroform (200 ml) and the solution washed successively with 200 ml portions of ice cold 0.1 N hydrochloric acid, 0.1 N sodium hydroxide and water. After drying the solvent was removed in vacuo and the residue crystallized from chloroform-ether to afford 1.37 g (73%), m.p. 146°–147° C.; $[\alpha]_D^{21}$ −54° (CHCl$_3$). Calc'd (C$_{23}$H$_{27}$NO$_5$): C, 69.5; H, 6.85; N, 3.52. Found: C, 69.2; H, 6.91; N, 3.43.

Steps 6–7. 4-Oxo-5-benzamido-6-phenylhexanoic acid (7)

A solution of 5 (1.30 g, 3.27 mmol) in acetone (325 ml) was cooled to 0°–5° C. and treated with chromium trioxide (3.27 g, 32.7 mmol) in 35% sulfuric acid (100 ml). After 1 hour the green solution was partitioned between chloroform (650 ml) and water (650 ml). The chloroform solution was washed with water (650 ml), dried and evaporated to leave 1.17 g of crude 6 as a white foam. A solution of the foam in 90% trifluoroacetic acid (10 ml) was kept for 16 hours at ambient temperature and evaporated. A chloroform solution (120 ml) of the residue was washed with water (120 ml), dried and evaporated to leave 1.18 g of a white foam. Crystallization from chloroform-ether afforded 0.54 g, m.p. 141.5°–142.5° C.; $[\alpha]_D^{21}$ +38.9° (CHCl$_3$); Calc'd (C$_{19}$H$_{19}$NO$_4$): C, 70.1; H, 5.88; N, 4.30. Found: C, 69.9; H, 6.10; N, 4.19. Retreatment of the mother liquor with 90% trifluoroacetic acid gave another 0.25 g, m.p. 140.5°–141.5° C., for a total yield of 74%.

Step 8. 4-Oxo-5-benzamido-6-phenylhexanoyl-L-proline benzyl ester (8).

A stirred mixture of 7 (5.90 g, 18.1 mmol), L-proline benzyl ester (4.38 g, 18.1 mmol), 1-hydroxybenzotriazole hydrate (2.77 g, 18.1 mmol), dichloromethane (270 ml) and triethylamine (2.51 ml, 18.1 mmol) was cooled to 0°–5° C. and dicyclohexylcarbodiimide (3.74 g, 18.1 mmol) in dichloromethane (25 ml) was added. After 3 days at ambient temperature the mixture was filtered and the filtrate diluted to 400 ml with dichloromethane. The solution was washed successively with 300-ml portions of 2 N hydrochloric acid, 0.3 N sodium hydroxide and water. The extract was dried, filtered and evaporated to dryness. Dissolution in ice cold ethyl acetate (25 ml) followed by filtration and reevaporation afforded 8.3 g of a foam. This material was purified by chromatography to yield 6.6 g (71%) of a white foam whose proton and $^{13}$C-NMR spectra were in agreement with the product 8. Calc'd. (C$_{31}$H$_{32}$N$_2$O$_5$): C, 72.6; H, 6.30; N, 5.46. Found: C, 71.6; H, 6.32; N, 5.42.

Step 9. 4-Oxo-5-benzamido-6-phenylhexanoyl-L-proline (9)

A mixture of 8 (5.24 g, 10.2 mmol), 10% palladium-on-carbon (5.24 g) and acetic acid (125 ml) was stirred under one atmosphere of hydrogen for 15 hours. The catalyst was removed by filtration and the solvent removed in vacuo to leave a syrup. The syrup was dissolved in acetone (25 ml), diluted with ethyl acetate (300 ml) and the solution washed with water (200 ml). The aqueous wash was extracted twice with 100-ml portions of ethyl acetate and the combined extracts dried and evaporated to leave 3.53 g of a white solid. Recrystallization from ethyl acetate yielded 3.10 g (72%), m.p. 151°–153° C.; $[\alpha]_D^{21}$ −83.2° (CHCl$_3$); Calc'd (C$_{24}$H$_{26}$N$_2$O$_5$): C, 68.2; H, 6.20; N, 6.63. Found: C, 68.2; H, 6.30; N, 6.52.

Procedure B

Step 1. 2-Phenyl-4-benzyloxazolone (10)

To a solution of 165 g of d,l-phenylalanine in 1100 ml of 1 N sodium hydroxide was added simultaneously 1000 ml of 1 N sodium hydroxide and 146 g of benzoyl chloride over a period of 1 hr with maintenance of the temperature at 2°–5° C. After 3 hr at 5°–10° C., the solution was acidified to pH4 with 5 N hydrochloric acid. The precipitate was collected, washed with water and acetone and dried to leave 234.5 g (87%) of N-benzoyl phenylalanine, mp 185°–188° C. The material was mixed with 2000 ml of acetic anhydride and heated at 95°–100° for 45 minutes. The solvent was removed in vacuo to afford 222 g (100%) of the azlactone, m.p. 60° C.

Step 2. 2-Phenyl-4-benzyl-4-β-carbomethoxypropionyloxazolone (11).

A mixture of 125 g of the azlactone above, 75 g of carbomethoxypropionyl chloride and 1000 ml of tetrahydrofuran was cooled to 0°–5° C. and treated dropwise with 75 ml of triethylamine. After 2 hr cooling was removed and the suspension allowed to stand at ambient temperature for 18 hr. The mixture was filtered and the filtrate evaporated in vacuo to give 185.5 g (100%) of the product which was carried directly into the next step.

Step 3. Methyl 5-Benzamido-4-oxo-6-phenylhexanoate (12).

A solution of 185.5 g of the crude acyl azlactone (11) in 600 ml of pyridine was heated to 80° and 450 ml of acetic acid was added causing evolution of carbon dioxide. Heating was continued at 90°–100° for one hr and the solvent evaporated in vacuo to leave 184 g of crude oxo ester. Recrystallization from isopropyl ether afforded 133 g. m.p. 90°–95° C. An analytical sample melted 94°–95° C. Calcd. (C$_{20}$H$_{21}$NO$_4$) C, 70.8; H, 6.24; N, 4.13. Found: C, 70.6; H, 6.10; N, 4.02.

Step 4. 5-Benzamido-4-oxo-6-phenylhexanoic acid (13). A solution of 132.5 g of the ester (12) in 1000 ml of tetrahydrofuran containing 900 ml of 0.5 N sodium hydroxide was kept at room temperature for 24 hr. The solvent tetrahydrofuran was evaporated in vacuo and the residual suspension was filtered. The filtrate was acidified with dilute hydrochloric acid and the precipitated product collected, washed with water and dried. Recrystallization from 95% ethanol yielded 96.4 g (76%) of white crystal, m.p. 182°–184°. Calcd. ($C_{19}H_{19}NO_4$): C, 70.1; H, 5.89; N, 4.31. Found: C, 69.8; H, 5.75; N, 4.11.

Coupling of the oxo acid (13) with L-proline could be carried out as in Steps 8 and 9 of procedure A or as described below in:

Step 5. N,O-Di-trimethylsilyl-L-proline. A mixture of 100.5 g of L-proline, 220 g of hexamethyl disilazane, 400 ml of acetonitrile and 2 ml of chlorotrimethylsilane was heated at reflux for 3.5 hr. Solvent was removed in vacuo and the residue distilled to afford 187 g (83%) of liquid product, b.p. 105°–100°/20 mm.

Step 6. 5-Benzamido-4-oxo-6-phenylhexanoyl-L-proline. (9) A mixture of 6.5 g of the oxo acid (13) and 150 ml of tetrahydrofuran was cooled to 0°–5° C. and treated with 3.5 g of carbonyldiimidazole. The mixture was stirred at 50° C. for 1 hr, cooled to 0°–5° C. and treated with 5.9 g of the silyl protected proline (from Step 5). The mixture was stirred at reflux for 5 hr and evaporated in vacuo. The residue was treated with 50 ml of water and the resulting solution was acidified to pH 4 with 1N hydrochloric acid. The gummy precipitate was extracted into chloroform, the extract washed thrice with water and evaporated to yield a foam. Crystallization from ethyl acetate afforded 5-benzamido-4-oxo-6-phenylhexanolyl-L-proline (9) identical in all respects with material prepared by Procedure A.

EXAMPLE II

Methyl 5-benzamido-4oxo-6-phenylhexanoyl-L-prolinate

A mixture of 0.60 g of the oxo acid (9), 0.31 g of L-proline methyl ester hydrochloride, 0.27 g of 1-hydroxybenztriazole hydrate, 0.26 ml of triethylamine and 40 ml of dichloromethane was cooled to 0°–5° and 0.38 g of dicyclohexylcarbodiimide was added. The mixture was stirred 2 days at room temperature, filtered and the filtrate was washed successively with 2N hydrochloric acid, 0.3 N sodium hydroxide and water. The extract was dried over magnesium sulfate and evaporated to dryness. The product was obtained from chloroform-ether, 0.68 g, m.p. 80°–87° C. Calcd. ($C_{25}H_{28}N_2O_5$) C, 68.8; H, 6.47; N, 6.42. Found: C, 68.6; H, 6.49; N, 6.29.

EXAMPLE III

5-Benzyloxycarbonylamino-4-oxo-6-phenylhexanoyl-L-proline

Step. 1. 5-Amino-4-oxo-6phenylhexanoic acid hydrochloride. (19)

A mixture of 3.3 g of 5-benzamido-4-oxo-6-phenylhexanoic acid (Step 4, Procedure B, Example I), 100 ml of concentrated hydrochloric acid, 50 ml of acetic acid and 50 ml of water was heated at reflux for 6 hr. The resulting solution was concentrated to dryness in vacuo, whereupon toluene (30 ml) was added and evaporated to remove residual water. The resulting gum was crystallized from acetonitrile to yield 1.5 g of product, m.p. 115° C. Drying at 80° under reduced pressure raised the melting point to 130° C. Calcd. ($C_{12}H_{16}NO_3Cl$)C, 55.9; H, 6.26; N, 5.44. Found: C, 56.0; H, 6.51; N, 5.39.

Step 2. Methyl-5-benzyloxycarbonylamino-4-oxo-6-phenyl hexanoate. (21) A solution of the 5-amino-4-oxo-6-phenylhexanoic acid hydrochloride (1.0 g) obtained in Step 1 in 30 ml of methanolic hydrogen chloride was allowed to stand for 24 hr at room temperature. Solvent was removed in vacuo and the residual oil (20) was dissolved in 30 ml of water. Benzyloxycarbonyl chloride was added and the pH was adjusted to and maintained at 6.5 by addition of 0.2 N sodium carbonate. After 20 min the resulting gummy precipitate was extracted into ether, dried over magnesium sulfate and evaporated. The residue was treated with hexane to afford white crystals, m.p. 64°–65° C. Calcd. ($C_{21}H_{23}NO_5$) C, 68.3; H, 6.29; N, 3.79. Found: C, 68.2H, 6.34; N, 3.70.

Step 3. 5-Benzyloxycarbonylamino-4-oxo-6-phenylhexanoic Acid. (22)

The methyl ester (0.5 g) obtained in Step 2 was dissolved in 10 ml of methanol containing 1 ml of 2 N sodium hydroxide. After 20 minutes the solution was diluted with 20 ml of water, acidified with 1 ml of 2 N hydrochloric acid and the methanol evaporated in vacuo. The resulting solid product was collected by filtration and dried. Recrystallization from ethyl acetate-petroleum (1:1) gave 0.45 g (94%), m.p. 116°–117° C. Calcd. ($C_{20}H_{21}NO_5$) C, 67.6; H, 5.95; N, 3.94. Found: C, 67.7H, 5.99; N, 3.89.

Step 4. 5-Benzyloxycarbonylamino-4-oxo-6-phenylhexanoyl-L-proline.

A solution of L-Proline methyl ester hydrochloride (2.3 g) in 30 ml of dimethylformamide was cooled to 10° C. and 1.4 g of triethyl amine was added. Triethylamine hydrochloride was removed by filtration and the filtrate treated with 1.8 g of hydroxybenzotriazole, 2.8 g of dicyclohexylcarbodiimide and 4.5 g of 5-benzyloxcarbonylamino-4-oxo-6-phenylhexanoic acid (Step 3). The reaction mixture was stirred for 2 days at ambient temperature and filtered. The filtrate was evaporated in vacuo and the residue dissolved in ehtyl acetate. The extract was washed with 1 Nsodium carbonate, dried over magnesium sulfate and evaporated to leave 7.0 g of the methyl ester as an oil.

The crude ester was dissolved in 30 ml of methanol and treated with 20 ml of 2 N sodium hydroxide. After 1 hr the solution was acidified with 20 ml of 2 N hydrochloric acid. Methanol was removed in vacuo and the aqueous residue extracted twice with 50 ml portions of ehtyl acetate. The extract was evaporated to an oil which was chromatographed on silica gel with elution by chloroform-methanol (95.5) to afford to 2.0 g whose infrared and nmr spectra were in agreement for the required product. The dicyclohexylamine salt, mp 60° C. was obtained by treatment of an ethyl acetate solution with an equivalent of dicyclohexylamine. Calc'd ($C_{25}H_{28}N_2O_6.\frac{1}{2}(C_{12}H_{23}N)$). C, 71.2; H, 8.76; N, 5.81. Found: C, 71.7; H, 8.94; N, 5.96.

EXAMPLE IV 5-(4-Pyridyl)carbonylamino-4-oxo-6-phenylhexanoyl-L-proline

The procedure used in Example III was followed except that isonicotinoyl azide was used in place of benzyloxycarbonyl chloride. The azide reagent was generated in situ by reaction of isonicotinoyl hydrazide and sodium nitrite in a slight excess in 1 N hydrochloric acid. The final product was obtained as an off-white solid, mp 100°–105° C. Calcd. ($C_{23}H_{25}N_3O_5$) C, 65.2; H, 5.95; N, 9.91. Found: C, 65.9; H, 5.90; N, 9.75.

EXAMPLE V 5-(2-Furoylamino)-4-oxo-6-phenylhexanoyl-L-proline.

2-(2-Furyl)-4-benzyloxazolone was prepared as in Step 1 of Example I, Procedure B except that 2-furoyl chloride was used in place of benzoyl chloride. The azlactone was carried through the remaining steps as in Example I, Procedure B to afford the final product as white crystals from ethyl acetate, mp 159°–161° C.; $[\alpha]_D^{23}$-85.3° (1% in CHCl$_3$). Calcd. (C$_{22}$H$_{24}$N$_2$O$_6$) C, 64.1; H, 5.87; N, 6.79. Found: C, 64.1; H, 5.78; N, 6.72.

EXAMPLE VI 5-(2-Tetrahydrofuroylamino)-4-oxo-6-phenylhexanoyl-L-proline.

A mixture of the furoyl compound (Example V), 10% palladium-on-carbon and methanol was shaken under a hydrogen atmosphere at 50 psi for 24 hr. The catalyst was removed by filtration and the solvent removed under reduced pressure to afford the product as a white solid, m.p. 40° C., $[\alpha]_D^{23}$-77°(1% in CHCl$_3$). Calc'd (C$_{22}$H$_{28}$N$_2$O$_6$.½H$_2$O). C, 62.1; H, 6.87; N, 6.59. Found: C, 62.3; H, 6.81; N, 6.34.

EXAMPLE VII

5-O-Toluoylamino-4-oxo-6-phenylhexanoyl-L-proline.

2-O-Tolyl-4-benzyloxazolone was prepared as in Step 1, Example I, Procedure B except that O-toluoyl chloride was used in place of benzoyl chloride. The azlactone was carried through the remaining steps as in Example I, Procedure B to afford the final product as white crystals, m.p. 150°–158° C. $[\alpha]_D^{23}$-75.0 (1% in CHCl$_3$). Calc'd (C$_{25}$H$_{28}$N$_2$O$_5$). C, 68.8; H, 6.47; N, 6.42. Found: C, 68.5; H, 6.41; N, 6.23.

EXAMPLE VIII

5-Benzamido-4-oxo-6-(3,4-dimethoxyphenyl)hexanoyl-L-proline.

2-Phenyl-4-(3,4-dimethoxybenzyl)oxazolone was prepared as in Step 1, Example I, Procedure B, except that 3,4-dimethoxyphenylalanine was used in palace of phenylalanine. The azlactone, mp 78°–80° C., was recrystallized from isopropyl ether. Calcd. (C$_{18}$H$_{17}$NO$_4$) C, 69.4; H, 5.51; N, 4.50. Found: C, 69.5; H, 5.47; N, 4.34.

The azlactone was carried through the remaining steps as in Example I, Procedure B to yield the final product as white crystals after chromatography on silica gel with elution by ethyl acetate, mp 75°–80° C.; $[\alpha]_D^{23}$-63.5° (1% in CHCl$_3$). Calcd. (C$_{26}$H$_{30}$N$_2$O$_7$) C, 64.7; H, 6.27; N, 5.81. Found: C, 64.5; H, 6.12; N, 5.63.

EXAMPLE IX

5-Benzamido-4-oxo-6-p-benzyloxyphenylhexanoyl-L-proline.

Step 1. 2-Phenyl-4-p-benzyloxybenzyloxazolone was prepared as in Step 1, Example I, Procedure B except that p-benzyloxyphenylalanine was used as the starting material in place of phenylalanine. The azlactone was obtained as a crystalline material from isopropyl ether and used directly in the next step. Completion of subsequent steps through Step 4 as in Example I, Procedure B afforded 5-benzamido-4-oxo-6-p-benzyloxyphenylhexanoic acid, mp 146°–149° C., after crystallization from ethanol. Calcd. (C$_{26}$H$_{25}$NO$_5$) C, 72.4; H, 5.84; N, 3.25. Found: C, 72.3; H, 5.91; N, 3.22.

Step 2. The hexanoic acid intermediate above was coupled with L-proline benzyl ester via the procedure described in Step 8, Example I, Procedure A to afford 5-benzamido-4-oxo-6-p-benzyloxphenylhexanoyl-L-proline benzyl ester, mp 52°–55°. Calcd. (C$_{38}$H$_{38}$N$_2$O$_6$) C, 73.8; H, 6.14; N, 4.53. Found: C, 73.8; H, 6.11; N, 4.55.

Step 3. Saponification of the benzyl ester via the procedure described for hydrolysis of a proline methyl ester in Step 4, Example III gave the required product, mp 70°–78° C., $[\alpha]_D^{23}$-56.6(1% in CHCl$_3$) Calc'd (C$_{31}$H$_{32}$N$_2$O$_6$.H$_2$O). C, 68.1; H, 6.27; N, 5.12. Found: C, 68.5; H, 6.07; N, 5.25.

EXAMPLE X

5-Benzamido-4-oxo-6-p-hydroxyphenylhexanoyl-L-proline

A mixture of 4.0 g of the benzyl ester (Step 2, Example IX). 0.5 g of 20% palladium-on-carbon and 100 ml of methanol was stirred under an atmosphere of hydrogen for 4 hr. The catalyst was removed by filtration and the filtrate was evaporated to leave 2.5 g of product as white crystals, mp 113°–116°. Calcd. (C$_{24}$H$_{26}$N$_2$O$_6$). C, 65.7; H, 5.98; N, 6.38. Found: C, 65.6; H, 6.07; N, 6.49.

EXAMPLE XI

5-Benzamido-4-oxo-6-(3-pyridyl)hexanoyl-L-proline.

Step 1. 2-Phenyl-4-(3-pyridylmethyl)oxazolone. A mixture of 180 g of N-benzoyl glycine, 40 g of potassium bicarbonate and 400 ml of acetic anhydride was stirred until solution occurred. 3-Pyridylaldehyde (100 ml) was then added and the mixture stirred for 1 hr with maintenance of the temperature at 20°–25° C. by means of a cold water bath. The mixture was poured into 2 liters of hot water and the precipitate collected by filtration and dried to afford 2-phenyl-4-(3-pyridylmethylene)-2-oxazolin-5-one, mp 164.5° C. The material was hydrogenated in tetrahydrofuran solution over 20% palladium-on-carbon. The catalyst was removed by filtration and the solvent evaporated in vacuo to give the azlactone as a tan foam.

Step 2. 5-Benzamido-4-oxo-6-(3-pyridyl)hexanoic acid. The azlactone was converted to the intermediate oxo hexanoic acid by the procedure described in Steps 2–4, Example I, Procedure B. The acid was crystallized from isopropanol, mp 190°–192° C. Calcd (C$_{18}$H$_{18}$N$_2$O$_4$) C, 66.2; H, 5.56N, 8.59. Found: C, 66.0; H, 5.58; N, 8.48.

Step 3. 5-Benzamido-4-oxo-6-(3-pyridyl)hexanoyl-L-proline. The oxohexanoic acid obtained from Step 2 was coupled with L-proline benzylester as in Step 2, Example IX. The benzyl ester was removed by hydrogenation in methanol over 20% palladium-on-carbon. After removal of catalyst the filtrate was evaporated to yield the product, mp 80°–100°; $[\alpha]_D^{23}$-58.4° (1% in CHCl$_3$). Calcd. (C$_{23}$H$_{25}$N$_3$O$_5$.½H$_2$O) C, 63.9; H, 6.06; N, 9.71. Found: C 63.9; H, 5.98; N, 9.86.

EXAMPLE XII

5-Benzamido-4-oxo-6-phenylhexanoyl-L-hydroxyproline

5-Benzamido-4-oxo-6-phenylhexanoic acid, Step 4, Example I, Procedure B, was coupled with L-hydroxyproline methyl ester via the method described in Example II for the analogous proline ester. The ester was saponified via the procedure for hydrolysis of a proline methyl ester described in Step 4, Example III. The product was obtained as a white solid, m.p. 83°–101° C.; $[\alpha]_D^{23} -0.98°$ (1% in CH$_3$OH)

Calc'd (C$_{24}$H$_{26}$N$_2$O$_6$.⅛CHCl$_3$). C, 63.9; H, 5.81; N, 6.17. Found: C, 64.0; H, 5.58; N, 5.78.

EXAMPLE XIII

5-Benzamido-4-oxo-2-methyl-6-phenylhexanoyl-L-proline

Step 1. 2-Methyl succinic acid 1-methyl ester (3-carbomethyoxybutyric acid). To a solution of lithium amide (from 6.12 g of lithium) in liquid ammonia (1.5 liter) at −78° was added 39.6 g monomethyl succinate in 500 ml of ether. The mixture was stirred at the reflux temperature of ammonia for 1 hr when 42.6 g of methyl iodide in 400 ml of ether was added. The mixture was stirred at reflux temperature for 4 hr and then treated with 53 g of ammonium chloride by slow addition. Ammonia was allowed to evaporate and 300 g of ice was added followed by 450 ml of 3 N hydrochloric acid. The aqueus solution (pH 3) was decolorized with a little sodium bisulfite and then extracted with three 600-ml portions of chloroform. The extract was dried over magnesium sulfate and concentrated in vacuo to 17.8 g (41%) of an oil identified as the product by its nmr spectrum; (in CDCl$_3$) δ 1.22 (3H, d, CH$_3$), 2.00–3.20 (3H, m, CH$_2$ and CH), 3.70 (3H, s, OCH$_3$).

Step 2. 3-Carbomethoxybutyryl chloride. A mixture of 24.0 g of the acid ester (Step 1), 17.5 ml of oxalyl chloride and 40 ml of benzene was stirred at 40° C. under nitrogen for 3 hr. Solvent was removed in vacuo and the residual oil distilled at 0.75 mm Hg with collection of fractions boiling at 42°–46° C. to afford 21.0 g (78%); nmr (CDCl$_3$); δ 1.22 (3H, d, CH$_3$), 2.70–350 (3H, m, CH$_3$ and CH), 3.70 (3H, s, OCH$_3$).

Step 3. Methyl 5-benzamido-4-oxo-2-methyl-6-phenylhexanoate. The acid chloride above (Step 2) was used to acylate 2-phenyl-4-benzyloxazolone (Step 1, Example I, Procedure B) by the general procedure described in Step 2, Example I, Procedure B. The product was then decarboxylated as in Step 3 of Example I, Procedure B to afford methyl 5-benzamido-4-oxo-2-methyl-6-phenylhexanoate, m.p. 97°–98.5° C., after preparative liquid chromatography on silica gel with elution by ethyl acetate-petroleum ether (15:85). Calcd. (C$_{21}$H$_{23}$NO$_4$) C, 71.4; H, 6.56; N, 3.96. Found: C, 71.4; H, 6.52; N, 4.05.

Step 4. 5-Benzamido-4-oxo-3-methyl-6-phenylhexanoic acid. The ester from Step 3 was saponified in the manner described in Step 4, Example I, Procedure B to afford the acid product, m.p. 132°–134° C., as white crystals from aqueous ethanol. Calc'd (C$_{20}$H$_{21}$NO$_4$) C, 70.8; H, 6.24; N, 4.13. Found: C, 70.7; H, 6.13; N, 4.15.

Step 5. 5-Benzamido-4-oxo-2-methyl-6-phenylhexanoyl -L-proline.

The oxo hexanoyl acid from Step 4 was coupled with the benzyl ester of L-proline by the general method described in Step 8, Example I, Procedure A. The mixture of diastereomeric proline esters so obtained was separated by preparative liquid chromatography on silica gel with elution by ethyl acetate-petroleum ether-isopropanol (74:22:4). Four distinct isomers were obtained and identified by their nmr spectra, showing only subtle differences from one another in the spectra. Each ester was hydrogenated individually over 10% palladium-on-carbon in acetic acid as in Step 9, Example I, Procedure A to afford 4 stereoisomeric oxo hexanoyl prolines as white solids:

(a) $[\alpha]_D^{22°} -50.2°$ (1.1%, CHCl$_3$); +25.0° (1.0%, 95% C$_2$H$_5$OH) Calcd. (C$_{25}$H$_{28}$N$_2$O$_5$.¾ H$_2$O) C, 66.7; H, 6.60; N, 6.22. Found: C, 66.8; H, 6.36; N, 6.13

(b) $[\alpha]_D^{22°} -46.9°$ (1.0, CHCl$_3$); −102° (1.0, 95% C$_2$H$_5$OH) Calcd. (C$_{25}$H$_{28}$N$_2$O$_5$.½ H$_2$O) C, 67.4; H, 6.55; N, 6.28. Found: C, 67.3; H, 6.33; N, 6.16.

(c) $[\alpha]_D^{22°} -90.6°$ (1.1, CHCl$_3$); −113° (1.1, Ch$_2$H$_5$OH) Calcd. (C$_{25}$H$_{28}$N$_2$O$_5$.½ H$_2$O) C, 67.4; H, 6.55; N, 6.28 Found: C, 67.1; H, 6.33; N, 6.14.

(d) $[\alpha]_D^{22°} -97.7°$ (1.1, CHCl$_3$); +9.8° (1.0, C$_2$H$_5$OH) Calcd. (C$_{25}$H$_{28}$N$_2$O$_5$.1½ H$_2$O) C, 64.7; H, 6.73; N, 6.04. Found: C, 64.5, H, 6.16; N, 5.78.

EXAMPLE XIV

5-Benzamido-4-oxo-2-isopropyl-6-phenylhexanoyl-L-proline

Step 1. 2-Isopropylsuccinic acid 1-ethyl ester. To a stirred suspension of sodium hydride (16 g of 50% oil suspension) and 200 ml of benzene was added a small portion of a solution of acetone (9.6 g) in diethyl succinate (80 g). Ethanol (10 drops) was then added to start the reaction and the remainder of the acetone-succinate solution was added dropwise so as to prevent the reaction from becoming too vigorous. The resulting thick slurry was stirred for an additional 15 minutes and mixed with 400 ml of ice water. The organic layer was discarded and the aqueous was washed with three 150-ml portions of ether. The aqueus portion was acidified with 12 N hydrochloric acid and thrice extracted with 300-ml portions of benzene. The extract was dried over magnesium sulfate and evaporated to leave a semi-solid yellow residue. Crystallization from petroleum ether (b.p. 35°–60° C.); afforded 23.6 g (76%) of yellow crystals, m.p. 35°–40°, regarded as 2-isopropylidinesuccinic acid 1-ethyl ester. The ester acid was hydrogenated over platinum oxide in ethanol to yield 23 g of 2-isopropylsuccinic acid 1-ethyl ester as an oil; nmr (CDCl$_3$) δ 0.95 (6H, d, isopropyl CH$_3$), 1.27 (3H, t, ethyl CH$_3$), 1.77–2.97 (2H, m, CH's), 2.60 (2H, d, CH$_2$), 4.10 (2H, q, —OCH$_2$—).

Step 2. 5-Benzamido-4-oxo-2-isopropyl-6-phenylhexanoyl-L-proline.

The 2-isopropylsuccinic acid 1-ethyl ester was converted into the 4-acid chloride as in Step 2, Example XIII and condensed with 2-phenyl-4-benzyloxazolone, and the resultant product subsequently was decarboxylated and hydrolyzed to 5-benzamido-4-oxo-2-isopropyl-6-phenylhexanoic acid as in Steps 3–4, Example XIII. The intermediate hexanoic acid was condensed with L-proline benzyl ester in a manner similar to Step 8, Example I, Procedure A, except that 1-hydroxybenzotriazole was omitted. The resultant mixture of diastereomeric proline benzyl esters was hydrogenated over 10% palladium-on-carbon in 90% yield to afford 5-benzamido-4-oxo-2-isopropyl-6-phenylhexanoyl-L-proline as a isomeric mixture whose mass spectrum showed a peak at m/e 464 in agreement with the calculated molecular weight. Calcd (C$_{27}$H$_{32}$N$_2$O$_5$.H$_2$O) C, 67.2; H, 7.10; N, 5.80. Found: C, 66.8; H, 6.60; N, 5.90.

EXAMPLE XV 5-n-Butyloxycarbonylamino-4-oxo-6-phenylhexanoyl-L-proline

The procedure used in Example III was followed except that n-butoxycarbonyl chloride was used in place of benzyloxycarbonyl chloride. The dicyclohexylamine salt of the final product was obtained as a light tan solid, m.p. 85°–95° C. Calcd. ($C_{22}H_{30}N_2O_6 \cdot C_{12}H_{23}N$). Found: C, 67.6; H, 8.45; N, 6.84; C, 68.1; H, 8.90; N, 7.00.

EXAMPLE XVI

Methyl-5-n-butyloxycarbonylamino-4-oxo-2-methyl-6-phenylhexanoyl-L-proline

Step 1. Methyl 5-n-butyloxycarbonylamino-4-oxo-2-methyl-6-phenylhexanoate. 5-Benzamido-4-oxo-2-methyl-6-phenylhexanoic acid (Step 4, Example XV) was hydrolyzed to the 5-amino-4-oxo acid by the method used for Step 1, Example III. The amino oxo acid was converted to its methyl ester and acylated as in Step 2 of Example III except that n-butyloxycarbonyl chloride was used in place of benzyloxycarbonyl chloride. The methyl 5-n-butyloxycarbonylamino-4-oxo-2-methyl-6-phenylhexanoate was obtained as a yellow oil in 65% overall yield. Calcd. ($C_{19}H_{27}NO_5$) C, 65.3; H, 7.79; N, 4.01. Found: C, 65.3; H, 7.57; N, 3.91.

Step 2. 5-n-Butyloxycarbonylamino-4-oxo-2-methyl-6-phenylhexanoic acid. The acid was obtained as a yellow syrup by hydrolysis of the ester from Step 1 via the method described in Step 3, Example III. Calcd. ($C_{18}H_{25}NO_5$) C, 64.5; H, 7.51; N, 4.18. Found: C, 64.2; H, 7.43; N, 4.03.

Step 3. 5-n-Butyloxycarbonylamino-4-oxo-2-methyl-6-phenylhexanoyl-L-proline methyl ester.

Condensation of the acid from Step 2 with L-proline methyl ester was carried out as described in Step 4 of Example III, except that hydroxybenzotriazole was omitted. The product methyl ester was obtained as a yellow oil after purification by preparative liquid chromatography on silica gel using petroleum ether-ethylacetate-isopropanol (66:33:1) as eluant. Calcd. ($C_{24}H_{34}N_2O_6$) C, 64.5; H, 7.67; N, 6.27. Found: C, 64.3; H, 7.51; N, 6.03. The mass spectrum gave the correct mass, m/e 446.

EXAMPLE XVII 5-n-Butyloxycarbonylamino-4-oxo-2-methyl-6-phenylhexanoyl-L-proline The oxo hexanoic acid from Step 2, Example XVII was condensed with L-proline benzyl ester and the benzyl group removed by hydrogenation as in Step 8 and 9, Example I, Procedure A. The product was obtained in 89% yield as a clear oil; mass spectrum m/e 432 in agreement with the calculated molecular weight. Calcd. ($C_{23}H_{32}N_2O_6 \cdot \frac{1}{4} H_2O$) C, 63.2; H, 7.50; N, 6.40. Found: C, 63.1; H, 7.38; N, 6.28.

EXAMPLE XVIII

5-Acetylamino-4-oxo-6-phenylhexanoyl-L-proline

Step 1. 5-Acetylamino-4-oxo-6-phenylhexanoic acid. A solution of 2.57 g of 5-amino-4-oxo-6-phenyl-hexanoic acid hydrochloride (Step 1, Example III) in 100 ml of acetic acid containing 20 ml of water was cooled to 0°–5° C. and 5 ml of acetic anhydride and 1 g of sodium acetate was added. The mixture was stirred at 0°–5° C. for 2 hr, then allowed to stand at ambient temperature for 48 hr. The resulting solution was concentrated to dryness in vacuo and the residue dissolved in 10 ml of water. Upon addition of 1.5 g of potassium hydrogen sulfate a gummy product separated which was extracted into chloroform (50 ml). The extract was washed with 10 ml of cold water and evaporated in vacuo to yield 3 g of product, m.p. 127°–129° C. Calcd. ($C_{14}H_{17}NO_4$) C, 63.9; H, 6.51; N, 5.22. Found: C, 63.6; H, 6.48; N, 5.26.

the acetylamino acid obtained above in Step 1 was coupled with L-proline methyl ester and the intermediate saponified in the same manner as described in Step 4, Example III. The final product was obtained as white crystals from ethyl acetate, m.p. 156°–157° C. Calc'd ($C_{19}H_{24}N_2O_5$). C, 63.3; H, 6.71; N, 7.77. Found: C, 63.2; H, 6.44; N, 7.66.

EXAMPLE XIX 5-n-Hexanoylamino-4-oxo-6-phenylhexanoyl-L-proline

5-Amino-4-oxo-6-phenylhexanoic acid from Step 1. Example III was esterified with methanolic hydrogen chloride and acylated as in Step 2, Example III except that n-hexanoyl chloride was used instead of benzyloxycarbonyl chloride. The resultant methyl 5-n-hexanoyl-4-oxo-6-phenyl hexanoate was hydrolyzed as in Step 3, Example III and coupled with L-proline benzyl ester followed by hydrogenation as in Steps 8–9, Example I, Procedure A to afford the product, m.p. 138°–139° C.

EXAMPLE XX 5-n-Octanoylamino-4-oxo-6-phenylhexanoyl-L-proline.

The product was obtained in the same manner as described in Example XIX, except that n-octanoyl chloride was used instead of n-hexanoyl chloride, m.p. 137°–138° C. Calc'd ($C_{25}H_{36}N_2O_5$). C, 67.5; H, 8.16; N, 6.30. Found: C, 67.4; H, 8.07; N, 6.17.

EXAMPLE XXI 5-n-Decanoylamino-4-oxo-6-phenylhexanoyl-L-proline.

The product was obtained in the same manner as described for Example XIX except that n-decanoyl chloride was used instead of n-hexanoyl chloride, m.p. 139°–141° C. Calc'd ($C_{27}H_{40}N_2O_5$) C, 68.6; H, 8.53; N, 5.93. Found: C, 68.1; H, 8.45; N, 5.85.

It will be noted that the compounds of the present invention may be prepared in the form of their pharmaceutically acceptable (sterile) carboxylic acid or carboxylate salt derivatives. These salts may be formed via treatment of the carboxylic acid with, (1) suitable bases such as an alkali or alkaline earth metal hydroxide or alkoxide, for example, lithium hydroxide, sodium hydroxide, potassium hydroxide or calcium hydroxide; (2) with an alkali or alkaline earth metal carbonate or hydrogen carbonate, for example, sodium, potassium or calcium carbonate or bicarbonate; (3) with ammonia or various amines; or (4) with an ion exchange resin.

The compound of this invention, including the salts thereof, are effective when administered to animals by an available route, including, for example, oral and parenteral (intravenous, intraperitioneal, subcutaneous and intramuscular) administration. When used in this fashion, in effective amounts, said compounds inhibit angiotensin converting enzyme and, as such, are useful as antihypertensive agents.

BIOLOGICAL TESTS

The compounds of this invention were subjected to the Angiotensin Converting Enzyme Inhibition Assay, and activity in this assay against porcine-derived angiotensin converting enzyme is sufficient to consider a compound "active". Said assay is described in the literature as follows: B. S. Tsai, M. J. Peach, M. C. Khosla and F. M. Bumpus, entitled "Synthesis and Evaluation of [Des-Asp¹]angiotensin I as a Precursor for [Des-Asp¹]angiotensin II ("Angiotensin III"), "Journal of Medicinal Chemistry, 18, 1180–1183, (1975).

The Angiotensin Converting Enzyme Inhibition Assay represents a test procedure in which various compounds are tested for their ability to inhibit the conversion of the decapeptide angiotensin I or the tripeptide hippuryl-histidyl-leucine to its cleavage product, the dipeptide histidyl-leucine. This dipeptide is detected via its fluorescent condensation product with o-phthaladehyde. The condensation product, after stabilization by treatment with acid, is measured by excitation at 365 nm and emission at 495 nm in a fluorometer.

For testing the effect of inhibitors on procine plasma angiotensin-converting enzyme, two assays were run in parallel. One contained the substrate (1–2 mM), enzyme (1 mg) and various concentrations (1 nM–10 mM) of an inhibitor, the other contained only the substrate and enzyme. The assays were conducted in sodium phosphate buffer, pH 7.6, under the conditions described in the article by Tsai, et al., supra. The ratio of product formed with an inhibitor relative to that without an inhibitor was calculated to give the percent of inhibition for various concentrations of inhibitor. The $ID_{50}$ values are shown in the following Table II:

TABLE II

| Example | $ID_{50}$ nM |
| --- | --- |
| I | 3.2 |
| II | 82.0 |
| III | 240.00 |
| IV | 20.0 |
| V | 1.4 |
| VI | 20.0 |
| VII | 46.0 |
| VIII | 1.4 |
| IX | 10.0 |
| X | 4.7 |
| XI | 5.7 |
| XII | 540.0 |
| XIII (isomer - b) | 1.0 |
| XIV | 230.0 |
| XV | 210.0 |
| XVI | |
| XVII | 33.0 |
| XVIII | 330.0 |
| XIX | 47.0 |
| XX | 650.0 |
| XXI | 6500.0 |
| Captopril (Squibb) | 9.0 |

The term $ID_{50}$ refers to the dose of inhibitor sufficient to cause 50% inhibition of the conversion of substrate to product. In Table II the $ID_{50}$ values of Examples I-XXI and Captopril (Squibb) are shown. Several of the examples were more effective than Captopril in this assay, with Example XIII being the most effective compound.

What is claimed is:

1. Compounds having the structure

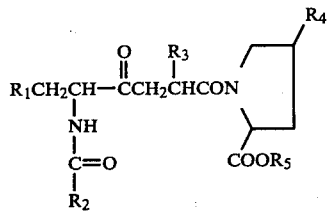

wherein
R₁ represents aryl;
R₂ represents aryl, alkyl or alkoxy;
R₃ represents hydrogen or lower alkyl;
R₄ represents hydrogen or hydroxyl; and
R₅ represents hydrogen or lower alkyl; and pharmaceutically acceptable salts of said compounds.

2. The compound of claim 1 which is 5-benzamido-4-oxo-6-phenylhexanoyl-L-proline, or its pharmaceutically acceptable salts.

3. The compound of claim 1 which is methyl 5-benzamido-4-oxo-6-phenylhexanoyl-L-prolinate, or its pharmaceutically acceptable salts.

4. The compound which is 5-benzyloxycarbonylamino-4-oxo-6-phenylhexanoyl-L-proline, or its parmaceutically acceptable salts.

5. The compound which is 5-(4-pyridyl)carbonylamino-4-oxo-6-phenylhexanoyl-L-proline, or its pharmaceutically acceptable salts.

6. The compound which is 5-(2-furoylamino)-4-oxo-6-phenylhexanoyl-L-proline, or its pharmaceutically acceptable salts.

7. The compound which is 5-(2-tetrahydrofuroylamino)-4-oxo-6-phenylhexanoyl-L-proline, or its pharmaceutically acceptable salts.

8. The compound which is 5-o-toluoylamino-4-oxo-6-phenylhexanoyl-L-proline, or its pharmaceutically acceptable salts.

9. The compound which is 5-benzamido-4-oxo-6-(3,4-dimethoxyphenyl)hexanoyl-L-proline, or its pharmaceutically acceptable salts.

10. The compound which is 5-benzamido-4-oxo-6-p-benzyloxyphenylhexanoyl-L-proline, or its pharmaceutically acceptable salts.

11. The compound which is 5-benzamido-4-oxo-6-p-hydroxyphenylhexanoyl-L-proline, or its pharmaceutically acceptable salts.

12. The compound which is 5-benzamido-4-oxo-6-(3-pyridyl)hexanoyl-L-proline, or its pharmaceutically acceptable salts.

13. The compound of claim 1 which is 5-benzamido-4-oxo-6-pphenylhexanoyl-L-hydroxyproline, or its pharmaceutically acceptable salts.

14. The compound of claim 1 which is 5-benzamido-4-oxo-2-methyl-6-phenylhexanoyl-L-proline, or its pharmaceutically acceptable salts.

15. The compound of claim 1 which is 5-benzamido-4-oxo-2-isopropyl-6-phenylhexanoyl-L-proline, or its pharmaceutically acceptable salts.

16. The compound of claim 1 which is 5-n-butyloxycarbonylamino-4-oxo-6-phenylhexanoyl-L-proline, together with its pharmaceutically acceptable salts.

17. The compound of claim 1 which is methyl 5-n-butyloxycarbonylamino-4-oxo-2-methyl-6-phenylhexanoyl-L-prolinate, or its pharmaceutically acceptable salts.

18. The compond of claim 1 which is 5n-butyloxycarbonylamino-4-oxo-2-methyl-6-phenylhexanoyl-L-proline, or its pharmaceutically acceptable salts.

19. The compound of claim 1 which is 5-acetylamino-4-oxo-6-phenylhexanoyl-L-proline, or its pharmaceutically acceptable salts.

20. The compound of claim 1 which is 5-n-hexanoylamino-4-oxo-6-phenylhexanoyl-L-proline, or its pharmaceutically acceptable salts.

21. The compound of claim 1 which is 5-n-octanoylamino-4-6-phenylhexanoyl-L-proline, or its pharmaceutically acceptable salts.

22. The compound of claim 1 which is 5-n-decanoylamino-4-oxo-6-phenylhexanoyl-L-proline, or its pharmaceutically acceptable salts.

* * * * *